United States Patent
Frumkin et al.

(10) Patent No.: US 11,952,632 B2
(45) Date of Patent: Apr. 9, 2024

(54) KITS AND METHODS FOR DETECTING CANCER-RELATED MUTATIONS

(71) Applicant: NUCLEIX LTD., Rehovot (IL)

(72) Inventors: Danny Frumkin, Rehovot (IL); Adam Wasserstrom, Ness Ziona (IL); Revital Knirsh, Rosh HaAyin (IL)

(73) Assignee: NUCLEIX LTD., Rehovot (IL)

( * ) Notice: Subject to any disclaimer, the term of this patent is extended or adjusted under 35 U.S.C. 154(b) by 909 days.

(21) Appl. No.: 16/959,557

(22) PCT Filed: Jan. 6, 2019

(86) PCT No.: PCT/IL2019/050027
§ 371 (c)(1),
(2) Date: Jul. 1, 2020

(87) PCT Pub. No.: WO2019/135241
PCT Pub. Date: Jul. 11, 2019

(65) Prior Publication Data
US 2020/0392586 A1    Dec. 17, 2020

Related U.S. Application Data

(60) Provisional application No. 62/614,421, filed on Jan. 7, 2018.

(51) Int. Cl.
| | | |
|---|---|---|
| C12P 19/34 | (2006.01) | |
| C12N 5/09 | (2010.01) | |
| C12N 15/10 | (2006.01) | |
| C12N 15/66 | (2006.01) | |
| C12Q 1/6827 | (2018.01) | |
| C12Q 1/6886 | (2018.01) | |
| G01N 33/574 | (2006.01) | |

(52) U.S. Cl.
CPC ......... C12Q 1/6886 (2013.01); C12N 5/0693 (2013.01); C12N 15/1089 (2013.01); C12N 15/66 (2013.01); C12Q 1/6827 (2013.01); G01N 33/574 (2013.01); *C12Q 2537/165* (2013.01); *C12Q 2565/40* (2013.01)

(58) Field of Classification Search
CPC ............................ C12Q 1/6851; C12Q 1/6886
See application file for complete search history.

(56) References Cited

U.S. PATENT DOCUMENTS

| 8,652,780 B2 | 2/2014 | Ehrich |
| 9,476,100 B1 | 10/2016 | Frumkin |
| 2011/0275073 A1 | 11/2011 | Gocke |

FOREIGN PATENT DOCUMENTS

| WO | 2011130636 A2 | 10/2011 |
| WO | 2013181276 A1 | 12/2013 |
| WO | 2015127168 A2 | 8/2015 |
| WO | 2017006317 A1 | 1/2017 |

OTHER PUBLICATIONS

Hengstler et al., (2000) Mutation analysis of the cationic trypsinogen gene in patients with pancreatic cancer. Anticancer Res 20(5A): 2967-2974.
Jenkins (2004) The restriction site mutation (RSM) method: clinical applications. Mutagenesis 19(1): 3-11.
Straughen et al., (1998) A rapid method for detecting the predominant Ashkenazi Jewish mutation in the Bloom's syndrome gene. Hum Mutat 11(2): 175-178.
Van Le et al., (1993) H-ras codon 12 mutation in cervical dysplasia. Gynecol Oncol 49(2): 181-184.
Asano et al., (2006) Detection of EGFR gene mutation in lung cancer by mutant-enriched polymerase chain reaction assay. Clin Cancer Res 12(1): 43-48.
Forbes et al., (2017) COSMIC: somatic cancer genetics at high-resolution. Nucleic Acids Res 45(D1): D777-D783.
Jenkins et al., (1999) The restriction site mutation assay: a review of the methodology development and the current status of the technique. Mutagenesis 14(5): 439-448.
Jenkins et al., (2002) Restriction enzymes in the analysis of genetic alterations responsible for cancer progression. Br J Surg 89(1): 8-20.
Lovly et al., (2015) EGFR c.2573T>G (L858R) Mutation in Non-Small Cell Lung Cancer. My Cancer Genome https://www.mycancergenome.org/content/disease/lung-cancer/egfr/5/ (Last updated: Oct. 15, 2015). Retrieved on Aug. 21, 2017. 4 pages.
Lovly et al., (2015) EGFR Exon 19 Deletion in Non-Small Cell Lung Cancer. My Cancer Genome https://www.mycancergenome.org/content/disease/lung-cancer/egfr/21/ (Last updated: Oct. 15, 2015). Retrieved on Aug. 21, 2017. 4 pages.
Prior et al., (2012) A comprehensive survey of Ras mutations in cancer. Cancer Res 72(10): 2457-2467.
Ward et al., (1998) Restriction endonuclease-mediated selective polymerase chain reaction: a novel assay for the detection of K-ras mutations in clinical samples. Am J Pathol 153(2): 373-379.
Zhao et al., (2013) Restriction endonuclease-mediated real-time digestion-PCR for somatic mutation detection. Int J Cancer 132(12): 2858-2866.

*Primary Examiner* — Kenneth R Horlick
(74) *Attorney, Agent, or Firm* — Acuity Law Group, PC; Michael A. Whittaker

(57) ABSTRACT

Methods and kits for detection of cancer-related mutations in a DNA sample using enzymatic restriction and real-time PCR. A DNA sample is subjected to digestion with a restriction endonuclease to obtain restriction endonuclease-treated DNA, followed by co-amplification of a restriction locus comprising a cancer mutation site and a control locus. A ratio of signal intensities of the amplification products of the restriction locus and the control locus is used to detect the cancer-related mutation.

20 Claims, 2 Drawing Sheets
Specification includes a Sequence Listing.

SEQUENCE LISTING

```
<160> NUMBER OF SEQ ID NOS: 6

<210> SEQ ID NO 1
<211> LENGTH: 23
<212> TYPE: DNA
<213> ORGANISM: Artificial Sequence
<220> FEATURE:
<223> OTHER INFORMATION: Primer

<400> SEQUENCE: 1
ggatcatatt cgtccacaaa atg                                              23

<210> SEQ ID NO 2
<211> LENGTH: 24
<212> TYPE: DNA
<213> ORGANISM: Artificial Sequence
<220> FEATURE:
<223> OTHER INFORMATION: Primer

<400> SEQUENCE: 2
tataaacttg tggtagttgg acct                                             24

<210> SEQ ID NO 3
<211> LENGTH: 92
<212> TYPE: DNA
<213> ORGANISM: Artificial Sequence
<220> FEATURE:
<223> OTHER INFORMATION: Polynucleotide

<400> SEQUENCE: 3
tataaacttg tggtagttgg acctggtggc gtaggcaaga gtgccttgac gatacagcta     60
```

```
attcagaatc attttgtgga cgaatatgat cc                                    92

<210> SEQ ID NO 4
<211> LENGTH: 77
<212> TYPE: DNA
<213> ORGANISM: Homo sapiens

<400> SEQUENCE: 4
agcaaggtga agactaactt ttctcttgta cagaatcatc aggctaaatt tttggcatta     60
tttcagtcct tggagac                                                    77

<210> SEQ ID NO 5
<211> LENGTH: 15
<212> TYPE: DNA
<213> ORGANISM: Homo sapiens

<400> SEQUENCE: 5
ggagctggtg gcgta                                                      15

<210> SEQ ID NO 6
<211> LENGTH: 9
<212> TYPE: DNA
<213> ORGANISM: Artificial Sequence
<220> FEATURE:
<223> OTHER INFORMATION: Polynucleotide

<400> SEQUENCE: 6 ggacctggt                                                              9
```

KITS AND METHODS FOR DETECTING CANCER-RELATED MUTATIONS

FIELD OF THE INVENTION

The present invention relates to detection of cancer-related mutations in DNA samples using enzymatic restriction and real-time PCR.

BACKGROUND OF THE INVENTION

Cancer is associated with alterations in genes encoding various cellular molecules. The spectrum of cancer mutations is diverse in terms of type, number and functional consequences. Examples include single base changes, deletions and alternative splicing or translocations. Specific mutations have been linked to one or more types of cancers, and mutant gene products have been associated with biological characteristics of cancer.

Mutational profiles of tumor DNA are important for patient management, including in diagnosis, prognosis and determination of treatment course. However, detecting cancer-related mutations in the clinical setting is challenging, as clinical samples typically contain only small amounts of mutated tumor genes within large amounts of normal genes. Detection of cancer-related mutations is particularly challenging when analyzing circulating tumor DNA (ctDNA) in a plasma sample. Thus, highly sensitive, yet specific, assays are needed.

Currently, clinical testing for most genetic variants is performed using technologies such as allele-specific polymerase chain reaction (PCR), Sanger dideoxy sequencing, pyrosequencing, multiplex ligation-dependent probe amplification (MLPA), or mass spectrometry (MS). Newer, next-generation sequencing (NGS) technologies, also known as massive parallel sequencing, are emerging. NGS enables amplification and sequencing of a large number of sequences in parallel. However, this technique is currently expensive and complicated for routine clinical testing.

Jenkins et al. (1999) *Mutagenesis*, 14(5):439-48 provide an overview of a methodology termed restriction site mutation assay for detecting mutations in ubiquitous restriction enzyme sites. Briefly, DNA mutations in ubiquitous restriction enzyme sites eliminate the ability of the restriction enzyme to recognize the specific DNA target sequence. Thus, wild type DNA is recognized and cleaved by the restriction enzyme, while DNA containing a mutation in the restriction enzyme site is not recognized by the restriction enzyme, remaining undigested and providing a substrate for subsequent PCR amplification. PCR amplification products are subjected to gel electrophoresis to detect enzyme-resistance bands, i.e., presence of mutation.

Jenkins et al. (2002) *Br J Surg.* 89(1):8-20 review methods that employ restriction enzymes in the analysis of genetic alterations responsible for cancer progression.

Ward et al. (1998) *Am J Pathol.*, 153(2): 373-379 report a strategy for enriched PCR, in which the concurrent activity of the restriction enzyme BstNI and Taq polymerase allowed the amplification of mutant K-ras while inhibiting the formation of wild-type product. This restriction endonuclease-mediated selective PCR assay uses three sets of primers, together with BstNI, in the reaction mix, and the amplification products are analyzed by gel electrophoresis.

Asano et al. (2006) *Clin Cancer Res*, 43:12(1), 43-48 report the development of a PCR-based assay for mutations in EGFR exons 19 and 21, and for detecting EGFR mutations in clinical samples, including specimens by biopsies, pleural fluid, and surgically resected tissues from patients with non-small cell lung cancer (NSCLC).

Zhao et al. (2013) *Int. J. Cancer,* 132, 2858-2866 report a method that couples PCR with restriction endonuclease digestion (designated real-time digestion-PCR, or RTD-PCR) in a one-step reaction tube for detecting somatic mutations from a minority of cells. The PCR mixture contains a thermostable restriction enzyme that digests wild-type alleles during the PCR program, allowing selective amplification of the mutant alleles.

WO 2013/181276 discloses compositions and methods for detecting rare nucleic acid molecule mutations in a plurality of nucleic acid molecules. Also disclosed are methods for determining the size of a nucleic acid molecule using droplet digital PCR.

Hitherto described methods have a number of drawbacks, where some are laborious and expensive and others are insufficiently sensitive and/or specific, and lack quantitative data or require complicated processing and calibrations in order to provide quantitative data.

There is a need for improved methods and kits for detecting cancer-related mutations in DNA samples, which are simple to operate, cost-effective and characterized by high specificity and sensitivity.

SUMMARY OF THE INVENTION

The present invention provides according to some aspects methods for detecting cancer-related mutations in DNA samples based on selective digestion of wild-type DNA while mutated DNA remains intact, followed by PCR amplification and analysis of amplification products. The PCR amplification involves co-amplification of two loci, one which remains intact if mutation is present and another which always remains intact under the test conditions and serves as a control. The disclosed methods involve calculating ratios between signal intensities of the amplification products of these loci and detecting cancer-related mutations based on the calculated ratios, resulting in highly accurate mutation detection. The DNA samples may originate from tumor tissues or plasma samples. Further provided are methods for determining whether a subject is positive for a cancer-related mutation.

In particular, the methods disclosed herein detect cancer-related mutations within restriction enzyme sites. Non-mutated (wild type) DNA comprises the restriction enzyme site and is recognized by the restriction enzyme. Non-mutated DNA is therefore cleaved upon contact with the restriction enzyme. In mutated DNA, the restriction enzyme site is altered and thus mutated DNA is not recognized by the restriction enzyme. Mutated DNA remains intact upon contact with the restriction enzyme, and provides a substrate for subsequent PCR amplification. Subsequent PCR amplification of a locus with the restriction enzyme site (a "restriction locus") which comprises the mutation position amplifies only mutated DNA, and enables determining the presence of mutation. In order to achieve high specificity, only mutation level above a certain threshold is considered clinically significant. It is therefore important to have a quantitative means to determine whether a DNA sample is considered positive for a certain mutation. The present invention advantageously addresses this need by co-amplification of a control locus that does not contain the recognition sequence of the restriction enzyme, and calculation of a ratio between signal intensities of amplification products of the restriction locus and the control locus. Different mutation levels result in different signal ratios between the restriction and control loci, where higher signal ratios correspond to higher mutation level. According to some embodiments, a threshold signal ratio is determined, above which a given DNA sample is identified as positive for a certain cancer-related mutation.

The present invention therefore provides simple, reliable means for detecting the presence of cancer-related mutations.

In some embodiments, the cancer mutation position (mutation site) is naturally found within a recognition sequence of a restriction enzyme (i.e., in native DNA). In other embodiments, the cancer mutation site is not naturally found within a recognition sequence of a restriction enzyme. According to these embodiments, in order to detect the mutation by the methods disclosed herein, a recognition sequence is artificially introduced by PCR. According to these embodiments, the DNA sample which is subjected to digestion and further analysis is a PCR product comprising an artificially-introduced restriction locus. In additional embodiments, the cancer mutation site is naturally found within a recognition sequence of a certain restriction enzyme, but a different restriction enzyme is desired for use with the methods of the present invention. The recognition sequence of the restriction enzyme of interest may be artificially introduced by PCR, and according to these embodiments the DNA sample which is subjected to digestion and further analysis is a PCR product comprising an artificially-introduced restriction locus.

For native DNA and native restriction loci, suitable loci comprise loci of restriction enzymes which are methylation-insensitive, so that digestion of the DNA will not be biased by the presence of methylation.

Thus, according to one aspect, the present invention provides a method for detecting a cancer-related mutation in a DNA sample, the method comprising:

a) subjecting the DNA sample to digestion with a restriction endonuclease to obtain restriction endonuclease-treated DNA;

(b) co-amplifying from the restriction endonuclease-treated DNA a restriction locus comprising a cancer mutation site, and a control locus, thereby generating an amplification product for each locus;

(c) calculating a ratio between signal intensities of the amplification products of the restriction locus and the control locus; and (d) detecting the cancer-related mutation in the DNA sample by comparing the ratio calculated in step (c) to a predefined threshold ratio.

In some embodiments, the cancer-related mutation is detected when the calculated ratio is above the predefined threshold ratio.

According to another aspect, the present invention provides a method for identifying a subject as positive for a cancer-related mutation, the method comprising:

(a) subjecting a DNA sample from the subject to digestion with a methylation-insensitive restriction endonuclease to obtain restriction endonuclease-treated DNA;

(b) co-amplifying from the restriction endonuclease-treated DNA a restriction locus comprising a cancer mutation site and a control locus, thereby generating an amplification product for each locus, (c) calculating a ratio between signal intensities of the amplification products of the restriction locus and the control locus; and (d) identifying the subject as positive for the cancer-related mutation by comparing the ratio calculated in step (c) to a predefined threshold ratio.

In some embodiments, the subject is identified as positive for the cancer-related mutation when the calculated ratio is above the predefined threshold ratio.

In some embodiments, the DNA originates from a tumor tissue.

In some embodiments, the DNA originates from plasma.

In some embodiments, the control locus is a locus devoid of the recognition sequence of said restriction endonuclease.

In some embodiments, the DNA is native DNA, the restriction locus is a native restriction locus, and the restriction endonuclease is a methylation-insensitive restriction endonuclease whose recognition sequence comprises the cancer mutation site.

In some embodiments, a cancer mutation whose site is naturally-found within the recognition sequence of a methylation-insensitive restriction endonuclease is selected from the group consisting of EGFR exon 19 deletion (E747-A750), EGFR L858 substitution, P53 H179 substitution, P53 G154 substitution, P53 R282 substitution, P53 R248 substitution, P53 8249 substitution and BRAF V600 substitution. Each possibility represents a separate embodiment of the present invention.

In some embodiments, the restriction endonuclease is selected from the group consisting of MseI (EGFR exon 19 deletion), MscI (EGFR L858 substitution), FatI (P53 H179 substitution), MspI (P53 G154 substitution, P53 8282 substitution, P53 R248 substitution), HaeIII (P53 R249 substitution) and TspRI (BRAF V600 substitution). Each possibility represents a separate embodiment of the present invention.

In other embodiments, the cancer mutation site is not naturally found within a recognition sequence of a restriction endonuclease. According to these embodiments, the DNA is a PCR product and the restriction locus is a restriction locus artificially-introduced into the DNA by said PCR.

In some embodiments, the cancer mutation whose site is not naturally found within a recognition sequence of a restriction endonuclease is selected from the group consisting of a KRAS G12 substitution and an EGFR L858 substitution. In some embodiments, the restriction endonuclease is selected from the group consisting of BtsIN (KRAS G12 substitution) and AluI (EGFR L858 substitution).

In some particular embodiments, the cancer mutation whose site is not naturally found within a recognition sequence of a restriction endonuclease is a KRAS G12 substitution and the restriction endonuclease is BtsIN. In some embodiments, the control locus is the locus set forth in SEQ ID NO: 4.

In some embodiments, the cancer-related mutation is selected from the group consisting of KRAS G12 substitution, EGFR exon 19 deletion (E747-A750), EGFR L858 substitution, P53 H179 substitution, P53 G154 substitution, P53 R282 substitution, P53 R248 substitution, P53 8249 substitution and BRAF V600 substitution. Each possibility represents a separate embodiment of the present invention.

In some embodiments, step (b) of the method is performed using real-time PCR. In some embodiments, when step (b) is performed using real-time PCR, the method further comprises adding fluorescent probes for assisting in detecting the amplification products of the restriction locus and the control locus.

In some embodiments, step (b) is performed using real-time PCR and said calculating a ratio between the signal intensities of the amplification products of said restriction locus and the control locus comprises determining the quantification cycle (Cq) for each locus and calculating $2^{(Cq\ control\ locus - Cq\ restriction\ locus)}$.

According to a further aspect, the present invention provides a kit for detecting cancer-related mutations in a DNA sample, the kit comprising:

at least one restriction endonuclease for digesting a DNA sample;

a plurality of primer pairs for co-amplification of at least one restriction locus comprising a cancer mutation site and at least one control locus following digestion with the restriction endonuclease; and a computer readable medium storing a computer software that directs a computer processor to detect a cancer-related mutation in the DNA sample based on a comparison of a ratio of signal intensities of the restriction locus and the control locus following amplification to a predefined threshold ratio.

In some embodiments, the computer software directs the computer processor to perform the following steps: determining signal intensities for the restriction locus and the control locus following their amplification; calculating a ratio between the signal intensities of the restriction locus and the control locus; comparing the calculated ratio to a predefined threshold ratio; and based on the comparison, outputting whether the DNA sample is positive for the cancer-related mutation.

In some embodiments, the kit further comprises a plurality of polynucleotide probes for detecting amplification products of the at least one restriction locus and the at least one control locus.

According to a further aspect, the present invention provides a system for detecting cancer-related mutations in a DNA sample, the system comprising:

at least one restriction endonuclease for digesting a DNA sample;

a plurality of primer pairs for co-amplification of at least one restriction locus comprising a cancer mutation site and at least one control locus following digestion with the restriction endonuclease; and computer software stored on a computer readable medium that directs a computer processor to detect a cancer-related mutation in the DNA sample based on a comparison of a ratio of signal intensities of the restriction locus and the control locus following amplification to a predefined threshold ratio.

In some embodiments, the computer software directs the computer processor to perform the following steps: determining signal intensities for the restriction locus and the control locus following their amplification; calculating a ratio between the signal intensities of the restriction locus and the control locus; comparing the calculated ratio to a predefined threshold ratio; and based on the comparison, outputting whether the DNA sample is positive for the cancer-related mutation.

These and further aspects and features of the present invention will become apparent from the detailed description, examples and claims which follow.

DETAILED DESCRIPTION OF THE INVENTION

Figure 1A:
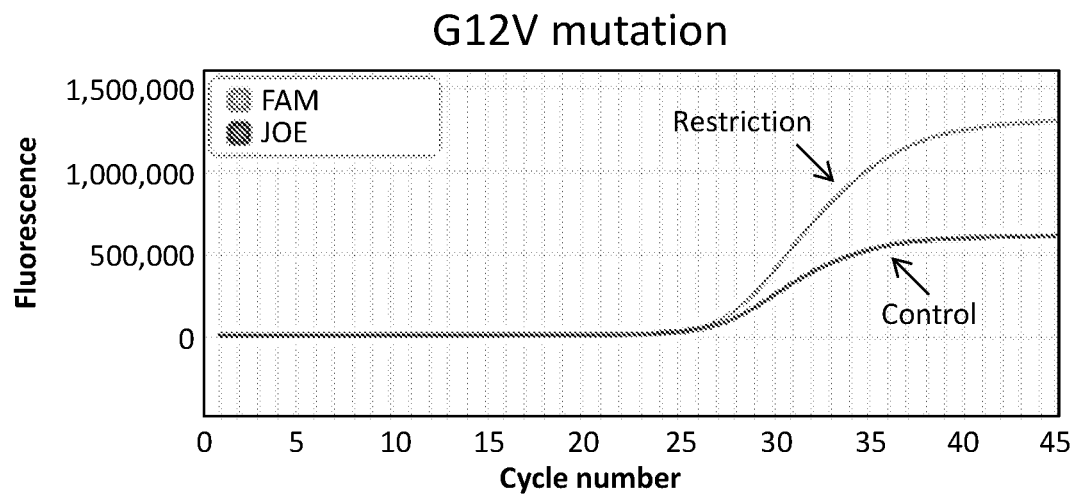
FIG. 1A-1D. Exemplary quantitative PCR plots of a restriction locus of BstNI comprising KRAS G12 mutation site and a control locus in DNA samples from cancerous lung tissues carrying: a G12V mutation (FIG. 1A), a G12A mutation (FIG. 1B) or no G12 mutation (FIG. 1C), and in a DNA sample from a normal lung tissue (no G12 mutation) (FIG. 1D)

The present invention relates to detection of mutations, particularly cancer-related mutations in DNA samples using enzymatic restriction and real-time PCR. The present invention involves calculating signal intensity ratios between a restriction locus comprising a mutation site (e.g., a cancer mutation site) and a control locus co-amplified from a tested DNA sample following digestion of the DNA with a restriction enzyme. Based on the signal intensity ratio, the tested sample is identified as positive or negative for the mutation (e.g., the cancer-related mutation).

The signal intensity ratios are calculated between loci amplified from the same DNA template in the same reaction mixture (i.e., under the same reaction conditions). This renders the methods disclosed herein insensitive to various "noise" factors, such as changes in template DNA concentration, PCR conditions, and presence of inhibitors.

Advantageously, according to some embodiments, the methods of the present invention are carried out without separating PCR products and/or sequencing. The methods of the present invention detect mutations with high specificity and sensitivity in a simple manner.

In addition, the present invention provides a simple means for identification of cancer-related mutations, which can be easily integrated into existing methods for cancer diagnosis, to provide at the same time diagnosis of the disease and information that can assist, for example, in selecting a suitable treatment and in determining disease prognosis. More particularly, the methods of the present invention may be integrated into cancer diagnosis methods such as the methods described in a co-pending application of the Applicant of the present invention directed to lung cancer diagnosis, and a co-pending application of the same Applicant directed to bladder cancer diagnosis. The methods disclosed therein comprise identifying cancer based on alterations in DNA methylation at selected genomic loci. The methods comprise digesting a DNA sample from a tested subject using a methylation-sensitive restriction endonuclease, co-amplifying at least one restriction locus differentially methylated between cancer and normal DNA and a control locus, and calculating signal intensity ratios of the restriction and control loci. The identification of cancer is carried out by comparing the calculated ratios to reference ratios. Advantageously, the method of the present invention, which is based on similar steps of DNA digestion followed by amplification, determination of signal intensities and calculating ratios, can be easily carried out in parallel to these diagnostic methods, to provide diagnosis and information about mutation status. For example, detection of lung cancer-related mutation(s) according to the present invention may be carried out in parallel to the aforementioned method of diagnosing lung cancer, to provide information whether the tested subject has lung cancer, and whether the subject bears one or more mutations that render the subject amenable to certain treatments, and/or affect the subject's prognosis.

In some embodiments, there is provided herein a method for detecting a cancer-related mutation in a DNA sample, the method comprising: (a) subjecting the DNA sample to digestion with a restriction endonuclease to obtain restriction endonuclease-treated DNA; (b) co-amplifying from the restriction endonuclease-treated DNA a restriction locus comprising a cancer mutation site and a control locus, thereby generating an amplification product for each locus; (c) calculating a ratio between signal intensities of the amplification products of the restriction locus and the control locus; and (d) determining whether the calculated ratio is above or below a predefined threshold ratio, thereby detecting the cancer-related mutation in the DNA sample.

In some embodiments, there is provided herein a method for generating a mutation profile in a DNA sample, the method comprising: (a) subjecting a DNA sample to digestion with a restriction endonuclease to obtain restriction endonuclease-treated DNA; (b) co-amplifying from the restriction endonuclease-treated DNA a restriction locus comprising a cancer mutation site and a control locus, thereby generating an amplification product for each locus; and (c) calculating a ratio between signal intensities of the amplification products of the restriction locus and the control locus. In some embodiments, the method further comprises determining whether the calculated ratio is above or below a predefined threshold ratio, thereby generating a mutation profile in the DNA sample.

In some embodiments, the methods comprise detecting the mutation on the basis of the ratio between signal intensities of the amplification products of the restriction locus and the control locus.

In some embodiments, the methods comprise detecting whether the mutation is present by calculating a ratio between signal intensities of the amplification products of the restriction locus and the control locus, and detecting a signal ratio above a predefined threshold ratio.

Biological Sample Collection and Processing

DNA to be analyzed may originate from a tumor tissue (solid tumor). DNA to be analyzed may also originate from a plasma sample.

The terms "DNA from", "DNA derived from", "DNA originates from" and the like refer to DNA obtained from a biological sample such as a tumor sample or a blood (plasma) sample. The terms encompass native DNA, that is, the DNA found in the biological sample, and also a PCR product generated from the native DNA, such as a PCR product comprising an artificially-introduced restriction locus.

Tumor and/or plasma samples may be collected from subjects using conventional methods.

The term "subject" as used herein is interchangeable with "individual" and typically refers to a human subject. The subject may be a cancer patient or suspected of having a cancer associated with a certain mutation. In some embodiments, the subject may be at risk of developing a cancer associated with a certain mutation, for example based on family history.

DNA may be extracted from the biological sample according to methods known in the art.

In some embodiments, when the cancer-related mutation is naturally-found within a restriction locus of a methylation-insensitive restriction enzyme, the native DNA obtained from the biological sample may be used for analysis of mutation status.

In other embodiments, when an artificial restriction locus is to be introduced, the native DNA obtained from the biological sample is subjected to PCR to introduce the restriction locus, prior to analysis of mutation status. In particular, PCR amplification of a locus comprising the cancer mutation site using mismatched primers is performed to introduce the artificial restriction locus. An exemplary procedure is exemplified hereinbelow.

DNA Digestion

According to the methods of the present invention, DNA from a biological sample or a PCR product generated from DNA from a biological sample is applied to digestion with a restriction endonuclease.

In some embodiments, the entire DNA that is extracted from a biological sample or generated by PCR is used in the digestion step. In some embodiments, the DNA is not quantified prior to being subjected to digestion. In other embodiments, the DNA is quantified prior to digestion thereof.

A "restriction endonuclease", used herein interchangeably with a "restriction enzyme", refers to an enzyme that cuts DNA at or near specific recognition nucleotide sequences, known as restriction sites.

A "methylation-insensitive" or "methylation-independent" restriction endonuclease is a restriction endonuclease whose activity is not affected by, or dependent on, the presence of methylation. In other words, a methylation-insensitive restriction endonuclease cleaves its restriction site independent of its methylation status.

The selection of a restriction endonuclease to be used by the methods of the present invention depends on the nucleotide sequence at or near the position of a cancer-related mutation to be detected. In some embodiments, when the mutation position is naturally found within the recognition sequence of a methylation-insensitive restriction endonuclease, this methylation-insensitive restriction endonuclease may be used. The digestion may be carried out on the native DNA from the biological sample.

In other embodiments, for example, when the mutation position is not within the recognition sequence of a methylation-insensitive restriction endonuclease, the restriction endonuclease may be selected based on technical criteria such as ability to work at high temperatures, and a proper recognition sequence may be introduced by PCR using mismatched primers. The restriction enzyme should preferably be other than methylation-dependent restriction enzyme. The digestion is carried out on the PCR product comprising the artificially-introduced recognition sequence.

Amplification of Genomic Loci

The terms "genomic locus" or "locus" as used herein are interchangeable and refer to a DNA sequence at a specific position on a chromosome. The specific position may be identified by the molecular location, namely, by the numbers of the starting and ending base pairs on the chromosome. A variant of a DNA sequence at a given genomic position is called an allele. Alleles of a locus are located at identical sites on homologous chromosomes. Loci include gene sequences as well as other genetic elements (e.g., intergenic sequences).

A "restriction locus" is used herein to describe a locus that contains the recognition sequence of the restriction enzyme that is used in the method.

A "restriction locus comprising a cancer mutation site" indicates a restriction locus comprising a position known to be prone to mutations in certain types of cancer. The cancer mutation site is located within the recognition sequence of the restriction enzyme used in the method. As a result of the DNA mutation, a mutated protein is generated, such as a protein in which a certain amino acid is substituted with another, or a protein in which one or more amino acids are deleted.

The term "cancer-related mutation" indicates a DNA mutation resulting in a mutated protein, which is associated with one or more types of cancers. The mutations are typically indicated by the name of the protein, the amino acid which is altered and its position (amino acid number) within the protein chain. For substitutions, the substituted amino acid is also typically indicated. Examples of cancer-related mutations include:

KRAS G12 substitutions: e.g. G12A, G12C, G12D, G12R, G12S and G12V, associated with cancers such as lung, pancreatic, bladder and colorectal cancer (reviewed, for example, in Prior et al. 2012, *Cancer Res.*, 72(10): 2457-2467).

EGFR exon 19 deletion (E747-A750 deletion): associated with cancers such as lung cancer, mainly non-small-cell lung cancer (NSCLC) (reviewed, for example, in Lovly et al. 2015, EGFR Exon 19 Deletion in Non-Small Cell Lung Cancer. My Cancer Genome (Updated Oct. 15, 2015).

EGFR L858 substitutions: e.g. L858R, associated with cancers such as lung cancer, mainly non-small-cell lung cancer (NSCLC) (reviewed, for example, in Lovly et al. 2015, EGFR c.2573T>G (L858R) Mutation in Non-Small Cell Lung Cancer. My Cancer Genome (Updated Oct. 15, 2015).

P53 H179 substitutions: e.g., H179R, H179L and H179Y, associated with cancers such as breast, ovarian and lung cancer (reviewed, for example, in COSMIC—the Catalogue of Somatic Mutations in Cancer (cancer.sanger.ac.uk) (Forbes et al. 2016, *Nucleic Acids Research*, 45(D1): D777-D783).

P53 G154 substitutions: e.g., G154V and G154S, associated with cancers such as lung, oesophagus and liver cancer (see COSMIC ibid.).

P53 R282 substitutions: e.g., R282W and R282G, associated with cancers such as intestine, oesophagus and breast cancer (see COSMIC ibid.).

P53 8248 substitutions: e.g., R248Q associated with cancers such as, colorectal, breast, oesophagus and CNS cancer, and lymphomas (see COSMIC ibid.).

P53 8249 substitutions: e.g., R249S, associated with cancers such as liver, lung and breast (see COSMIC ibid.).

BRAF V600 substitutions: e.g., V600E, associated with cancers such as thyroid and skin cancer (see COSMIC ibid.).

The terms "non-mutated DNA" and "wild type DNA" as used herein refer to the identity of the nucleotides at the cancer mutation site, where "non-mutated" and "wild type" indicates the presence of nucleotides which in vivo result in the translation of a proper wild-type protein.

The term "mutated DNA" refers to the identity of the nucleotides at the cancer mutation site, and indicates that it contains non-wild type nucleotides, associated with cancer.

A "control locus" and "internal reference locus" are interchangeable and used herein to describe a locus, the digestion of which with the restriction enzyme applied in the digestion step is independent of the presence or absence of mutation. Typically, the control locus is a locus devoid of the recognition sequence of the restriction enzyme applied in the digestion step. Advantageously, the control locus is an internal locus, i.e. a locus within the analyzed DNA sample, thus eliminating the need for external/additional control sample(s).

In a tissue positive for the mutation, a greater number of cells contain a mutation at this position compared to a tissue that is negative for the mutation. The restriction enzyme whose recognition sequence comprises the mutation site cleaves its recognition sequence only in non-mutated DNA. Thus, a DNA sample containing a higher percentage of DNA molecules with a mutation would be digested to a lesser extent compared to a DNA sample containing a higher percentage of non-mutated DNA. The difference in digestion efficiency establishes different amplification patterns in subsequent amplification and quantification steps, which enables distinguishing between DNA positive for the mutation and DNA negative for the mutation.

As used herein, "amplification" refers to an increase in the number of copies of one or more particular nucleic acid target of interest. Amplification is typically performed by polymerase chain reaction (PCR) in the presence of a PCR reaction mixture which may include a suitable buffer supplemented with the DNA template, polymerase (usually Taq Polymerase), dNTPs, primers and probes (as appropriate), as known in the art.

The term "polynucleotide" as used herein include polymeric forms of nucleotides of any length, either deoxyribonucleotides or ribonucleotides, or analogs thereof. The term "oligonucleotide" is also used herein to include a polymeric form of nucleotides, typically of up to 100 bases in length.

An "amplification product" collectively refers to nucleic acid molecules of a particular target sequence that are generated and accumulated in an amplification reaction. The term generally refers to nucleic acid molecules generated by PCR using a given set of amplification primers.

As used herein, a "primer" defines an oligonucleotide which is capable of annealing to (hybridizing with) a target sequence, thereby creating a double stranded region which can serve as an initiation point for DNA synthesis under suitable conditions. The terminology "primer pair" refers herein to a pair of oligonucleotides which are selected to be used together in amplifying a selected nucleic acid sequence by one of a number of types of amplification processes, preferably PCR. As commonly known in the art, the primers may be designed to bind to a complementary sequence under selected conditions.

As used herein a "mismatched primer" defines a primer that hybridizes partially to its corresponding target polynucleotide. A mismatched primer contains a complementary portion, and a non-complementary portion. The non-complementary portion of the mismatched primer is located at its 3' end, fails to hybridize with a nucleotide of interest present in a target polynucleotide, and is typically one nucleotide in length. Typically, the complementary portion of the mismatched primer is completely complementary to the target polynucleotide. The complementary portion can be any appropriate length. In some embodiments, the complementary portion is at least 6, at least 7, at least 8, at least 9, at least 10, at least 11, at least 12, at least 13, at least 14, at least 15, at least 15, at least 16, at least 17, at least 18, at least 19, or greater than 20 nucleotides in length.

The primers may be of any suitable length, depending on the particular assay format and the particular needs. In some embodiments, the primers may include at least 15 nucleotides in length, preferably between 19-25 nucleotides in length. The primers may be adapted to be especially suited to a chosen nucleic acid amplification system. As commonly known in the art, the oligonucleotide primers may be designed by taking into consideration the melting point of hybridization thereof with their targeted sequence.

In some embodiments, the restriction and control loci may be amplified from the same DNA sample (the digested sample) using pairs of reverse and forward primers designed as known in the art to specifically amplify each locus.

In some embodiments, the primers may be designed to generate amplification products of between 75-225 bases in length.

The methods disclosed herein involve simultaneous amplification of more than one target sequence (a restriction locus and a control locus) in the same reaction mixture, a process known as multiplex amplification or co-amplification. This process requires simultaneous use of two primer pairs. As known in the art, the primers may be designed such that they can work at the same annealing temperature during amplification. In some embodiments, primers with similar melting temperature (Tm) are used in the method disclosed herein. A Tm variation of between about 3°-5° C. is considered acceptable for primers used in a pool.

In some embodiments, amplification of the genomic loci may be carried out using Real-Time PCR (RT-PCR), also known as quantitative PCR (qPCR), in which simultaneous amplification and detection of the amplification products are performed.

In some embodiments, detection of the amplification products in RT-PCR may be achieved using polynucleotide probes, typically fluorescently-labeled polynucleotide probes.

As used herein, "polynucleotide probes" or "oligonucleotide probes" are interchangeable and refer to labeled polynucleotides which are complementary to specific sub-sequences within the nucleic acid sequences of loci of interest, for example, within the sequence of a restriction locus or a control locus. In some embodiments, detection is achieved by using TaqMan assays based on combined reporter and quencher molecules (Roche Molecular Systems Inc.). In such assays, the polynucleotide probes have a fluorescent moiety (fluorophore) attached to their 5' end and a quencher attached to the 3' end. During PCR amplification, the polynucleotide probes selectively hybridize to their target sequences on the template, and as the polymerase replicates the template it also cleaves the polynucleotide probes due to the polymerase's 5'-nuclease activity. When the polynucleotide probes are intact, the close proximity between the quencher and the fluorescent moiety normally results in a low level of background fluorescence. When the polynucleotide probes are cleaved, the quencher is decoupled from the fluorescent moiety, resulting in an increase of intensity of fluorescence. The fluorescent signal correlates with the amount of amplification products, i.e., the signal increases as the amplification products accumulate.

As used herein, "selectively hybridize to" (as well as "selective hybridization," "specifically hybridize to," and "specific hybridization") refers to the binding, duplexing, or hybridizing of a nucleic acid molecule (such as a primer or a probe) preferentially to a particular complementary nucleotide sequence under stringent conditions. The term "stringent conditions" refers to conditions under which a nucleic acid molecule will hybridize preferentially to its target sequence and to a lesser extent to, or not at all to, other non-target sequences. A "stringent hybridization" in the context of nucleic acid hybridization is sequence-dependent, and differs under different conditions, as known in the art.

Polynucleotide probes may vary in length. In some embodiments, the polynucleotide probes may include between 15-30 bases. In additional embodiments, the polynucleotide probes may include between 25-30 bases. In some embodiments, the polynucleotide probes may include between 20-30 bases, for example, 20 bases, 21 bases, 22 bases, 23 bases, 24 bases, 25 bases, 26 bases, 27 bases, 28 bases, 29 bases, 30 bases. Each possibility represents a separate embodiment of the present invention.

Polynucleotide probes may be designed to bind to either strand of the template. Additional considerations include the Tm of the polynucleotide probes, which should preferably be compatible to that of the primers. Computer software may be used for designing the primers and probes.

As noted above, the methods disclosed herein involve simultaneous amplification of more than one target sequence in the same reaction mixture. In order to distinguish between multiple target sequences that are amplified in parallel, polynucleotide probes labeled with distinct fluorescent colors may be used.

In some embodiments, the polynucleotide probes form a fluorophore/quencher pairs as known in the art and include, for example, FAM-TAMRA, FAM-BHQ1, Yakima Yellow-BHQ1, ATTO550-BHQ2 and ROX-BHQ2.

In some embodiments, the dye combinations may be compatible to the RT-PCR thermocycler of choice.

In some embodiments, fluorescence may be monitored during each PCR cycle, providing an amplification plot showing the change of fluorescent signals from the probes as a function of cycle number.

In the context of RT-PCR, the following terminology is used:

"Quantification cycle" ("Cq") refers to the cycle number in which fluorescence increases above a threshold, set automatically by software or manually by the user. In some embodiments, the threshold may be constant for all loci and may be set in advance, prior to carrying out the amplification and detection. In other embodiments, the threshold may be defined separately for each locus after the run, based on the maximum fluorescence level detected for this locus during the amplification cycles.

"Threshold" refers to a value of fluorescence used for Cq determination. In some embodiments, the threshold value may be a value above baseline fluorescence, and/or above background noise, and within the exponential growth phase of the amplification plot.

"Baseline" refers to the initial cycles of PCR where there is little to no change in fluorescence.

Computer software may be used to analyze amplification plots and determine baseline, threshold and Cq.

Following digestion with the restriction enzyme, loci in which the cancer mutation site is mutated are amplified with high efficiency, because the DNA molecules are protected from digestion. The result is relatively low Cq values because detectable amplification products are shown following a relatively small (low) number of amplification cycles. Conversely, loci in which the cancer mutation site is not mutated are cut more extensively during the digestion step, and thus result in higher Cq values in the amplification and quantification step (i.e., show detectable amplification products following a relatively high number of amplification cycles).

In alternative embodiments, amplification and detection of amplification products may be carried out by conventional PCR using fluorescently-labeled primers followed by capillary electrophoresis of amplification products. In some embodiments, following amplification, the amplification products are separated by capillary electrophoresis and fluorescent signals are quantified. In some embodiments, an electropherogram plotting the change in fluorescent signals as a function of size (bp) or time from injection may be generated, wherein each peak in the electropherogram corresponds to the amplification product of a single locus. The peak's height (provided for example using "relative fluorescent units", rFU) may represent the intensity of the signal from the amplified locus. Computer software may be used to detect peaks and calculate the fluorescence intensities (peak height) of a set of loci whose amplification products were run on the capillary electrophoresis machine, and subsequently the ratios between the signal intensities.

DNA samples digested with a restriction enzyme in which the cancer mutation site is mutated produce a relatively strong signal (higher peak) in the electropherogram. Conversely, loci in which the cancer mutation site is not mutated produce a relatively weak signal (lower peak) in the electropherogram.

In some embodiments, the fluorescent labels of the primers include any one of fluorescein, FAM, lissamine, phycoerythrin, rhodamine, Cy2, Cy3, Cy3.5, Cy5, Cy5.5, Cy7, FluorX, JOE, HEX, NED, VIC and ROX.

Signal Ratio

The term "ratio" or "signal ratio" as used herein refers to the ratio between the intensities of signals obtained from co-amplification of a pair of genomic loci in a single DNA sample (in the same reaction mixture), particularly co-amplification of a restriction locus and a control locus.

The term "signal intensity" as used herein refers to a measure reflecting the amount of locus-specific amplification products corresponding to the initial amount of intact copies of the locus. However, the signal intensity may not indicate actual amounts of amplification products/intact loci, and may not involve calculation of any absolute amounts of amplification products/intact loci. Thus, for calculating ratios of amplicon signals, no standard curve or reference DNA may be needed since it is unnecessary to calculate actual DNA concentrations per se.

In some exemplary embodiments, amplification and detection of amplification products are carried out by RT-PCR where the signal intensity of a specific locus is represented by the Cq calculated for this locus. The signal ratio in this case is represented by the following calculation:
$2^{(Cq\ of\ control\ locus - Cq\ of\ restriction\ locus)}$.

In some embodiments, in case of no amplification or very little amplification the Cq is determined as "infinity". In some embodiments, in such cases the numerical value of the equation (Cq of control locus−Cq of restriction locus) is set to be (−14) and the signal ratio is set to be 1:16384. In additional embodiments, in such cases the signal ratio is set to be 1:16000.

In additional exemplary embodiments, detection of amplification products is carried out by capillary electrophoresis wherein the signal intensity of a specific locus is the number of relative fluorescence units (rfus) of its corresponding peak. The signal ratio is calculated by dividing the heights of peaks of a restriction locus by the height of the peak of a control locus.

In some embodiments, calculating a ratio between signal intensities of the amplification products of a restriction locus and a control locus in a DNA sample comprises: (i) determining the signal intensity of the amplification product of the restriction locus; (ii) determining the signal intensity of the amplification product of the control locus; and (iii) calculating a ratio between the two signal intensities.

In some embodiments, calculating a ratio between signal intensities of the amplification products of a restriction locus and a control locus in the DNA sample comprises determining the Cq for each locus, and calculating the difference between the Cq of the control locus and the Cq of the restriction locus. In some embodiments, the calculating further comprises applying the following formula: $2^{\wedge}$(Cq of control locus−Cq of restriction locus).

In some embodiments, computer software may be used for calculating a ratio between signal intensities of amplification products.

Determining Mutation Status

The methods disclosed herein are based on evaluating a signal ratio calculated for a given DNA sample in order to determine its mutation status, namely whether it is positive or negative for a certain cancer-related mutation.

In some embodiments, a ratio calculated in a tested sample is compared to a reference ratio. In some embodiments, a calculated ratio is compared to a threshold ratio. In some embodiments, a calculated signal ratio indicates that the DNA is positive for the mutation when the calculated signal ratio is above or below a predefined threshold ratio.

A "threshold ratio" or "cutoff ratio" refers to a signal ratio that differentiates the population of mutation-negative samples from the population of mutation-positive samples.

In some embodiments, the lower ratios, below the threshold, are from non-mutated samples, e.g., samples of normal individuals (healthy, i.e., not afflicted with cancer), while the higher ratios above the threshold are from mutated samples, e.g., from cancer patients positive for the mutation.

In some embodiments, determining the threshold ratio includes measuring signal ratios between a certain pair of restriction and control loci in a large population of subjects (or biological samples) with a known mutation status, either mutation-positive or mutation-negative, as determined by other methods. After analysis of signal ratios in this large set of samples, the threshold is set to minimize false positive cases and obtain a desired level of specificity. Preferably, the threshold is set to obtain specificity above 95%.

As noted above, a signal ratio may be determined by various methods, including for example measuring peaks following capillary electrophoresis or calculating Cq following RT-PCR.

In some embodiments, the method of the present invention comprises providing a threshold ratio.

In some embodiments, the threshold values are statistically significant values. Statistical significance is often determined by comparing two or more populations, and determining a confidence interval (CI) and/or a p value. In some embodiments, the statistically significant values refer to confidence intervals (CI) of about 90%, 95%, 97.5%, 98%, 99%, 99.5%, 99.9% and 99.99%, while preferred p values are less than about 0.1, 0.05, 0.025, 0.02, 0.01, 0.005, 0.001 or less than 0.0001. Each possibility represents a separate embodiment of the present invention. According to some embodiments, the p value of the threshold value is at most 0.05.

As used herein, the term "about", when referring to a measurable value is meant to encompass variations of +/−10%, more preferably +/−5%, even more preferably +/−1%, and still more preferably +/−0.1% from the specified value.

In some embodiments, the sensitivity of the methods disclosed herein may be at least about 75%. In some embodiments, the sensitivity of the methods may be at least about 80%. In some embodiments, the sensitivity of the method may be at least about 85%. In some embodiments, the sensitivity of the methods may be at least about 90%.

In some embodiments, the "sensitivity" of a diagnostic assay as used herein refers to the percentage of mutated samples which test positive (percent of "true positives"). Accordingly, mutated individuals not detected by the assay are "false negatives". Samples which are not mutated and test negative in the assay are termed "true negatives." The "specificity" of the diagnostic assay is one (1) minus the false positive rate, where the "false positive" rate is defined as the proportion of those without the mutation who test positive. While a particular diagnostic method may not provide a definitive diagnosis of a condition, it suffices if the method provides a positive indication that aids in diagnosis.

In some embodiments, the specificity of the methods disclosed herein may be at least about 65%. In some embodiments, the specificity of the methods may be at least about 70%. In some embodiments, the specificity of the method may be at least about 75%. In some embodiments, the specificity of the methods may be at least about 80%.

Kits and Systems

In some embodiments, a kit is provided for detecting a cancer-related mutation in a DNA sample. In some embodiments, a system is provided for detecting a cancer-related mutation in a DNA sample.

In some embodiments, the kit and system are for detecting a cancer-related mutation according to the method of the present invention.

In some embodiments, the kit comprises: at least one restriction endonuclease for digesting a DNA sample and a plurality of primer pairs for co-amplification of at least one restriction locus comprising a cancer mutation site and at least one control locus, following digestion with the restriction endonuclease.

In some embodiments, the kit further comprises a computer readable medium storing a computer software that directs a computer processor to detect a cancer-related mutation in the DNA sample based on a comparison of a ratio of signal intensities of a restriction locus and its corresponding control locus following amplification to a predefined threshold ratio.

In some embodiments, the system comprises: at least one restriction endonuclease for digesting a DNA sample; a plurality of primer pairs for co-amplification of at least one restriction locus comprising a cancer mutation site and at least one control locus following digestion with the restriction endonuclease; and computer software stored on a computer readable medium that directs a computer processor to detect a cancer-related mutation in the DNA sample based on a comparison of a ratio of signal intensities of the restriction locus and the control locus following amplification to a predefined threshold ratio.

In some embodiments, a computer software according to the present invention directs a computer processor to perform the following steps: determining signal intensities for each restriction locus and each control locus following their co-amplification; calculating a ratio between the signal intensities of each restriction locus and its corresponding control locus; comparing the calculated ratio to a predefined threshold ratio; and based on the comparison, outputting whether the DNA sample is positive for the cancer-related mutation. In some embodiments, the kit or the system comprises primers for amplification of a single pair of restriction and control loci, to detect the presence of a single cancer-related mutation. In other embodiments, the kit or the system comprises primers for amplification of a plurality of restriction loci and corresponding control loci, to detect the presence of a plurality of cancer-related mutations.

In some embodiments, the computer software receives as an input parameters or raw data of a real-time PCR run. In some embodiments, the computer software directs a computer processor to analyze the real-time PCR run to determine signal intensities and signal ratios.

The computer software includes processor-executable instructions that are stored on a non-transitory computer readable medium. The computer software may also include stored data. The computer readable medium is a tangible computer readable medium, such as a compact disc (CD), magnetic storage, optical storage, random access memory (RAM), read only memory (ROM), or any other tangible medium.

In some embodiments, the kit comprises a restriction enzyme; pairs of primers for amplification of a restriction locus and a control locus; means for detecting amplification products of the restriction locus and the control locus; and instruction manual for carrying out the determination of the cancer-related mutation. In some embodiments, the instruction manual may be an electronic instruction manual.

In some embodiments, the instruction manual may provide a threshold signal ratio, above which a sample is determined to be mutation-positive. In other embodiments, the instruction manual may provide a threshold signal ratio, below which a sample is determined to be mutation-positive.

In some embodiments, the instruction manual may include instructions for performing the method steps described above.

In some embodiments, the instruction manual may include instructions directing the correlation between signal ratios and mutation status.

In some embodiments, the instruction manual may provide instructions for calculating a signal ratio.

In some embodiments, the kit comprises a methylation-insensitive endonuclease.

In some embodiments, the kit may further comprise a computer software. In some embodiments, the computer software may be a computer software that calculates at least one of signal intensities and signal ratios.

In some embodiments, the kit comprises fluorescent polynucleotide probes complementary to the restriction locus and the control locus.

In some embodiments, the kit comprises primer pairs complementary to the restriction locus and the control locus as described herein; and fluorescent polynucleotide probes complementary to a sub-sequence within the restriction locus and the control locus.

In some embodiments, the kit comprises mismatched primers for introducing an artificial restriction locus into the DNA sample.

In some embodiments, the kit comprises one or more containers filled with at least one nucleotide primer pair. In some embodiments, each nucleotide primer pair included in the kit of the present invention may include primers that are complementary to sub-sequences within a restriction locus or a control locus, wherein said each nucleotide primer pair is designed to selectively amplify a fragment of the genome that includes the restriction or control locus.

In some embodiments, the kit may comprise primer pairs for selectively amplifying the combination of loci described above.

In some embodiments, the kit may further include oligonucleotide probes for detecting amplification products of the loci amplified using the primers in the kit. Each oligonucleotide probe may be complementary to a sub-sequence within a locus and may be capable of hybridizing thereto. In some embodiments, the oligonucleotide probes may be fluorescently-labeled.

In some embodiments, the kit may further include at least one additional ingredient needed for DNA digestion, loci amplification and detection of amplification products, such as DNA polymerase and nucleotide mix.

In some embodiments, the kit may further include suitable reaction buffers for digestion and amplification, and a written protocol for performing mutation detection. The written protocol may comprise instructions for performing any of the steps disclosed herein, including but not limited to, DNA digestion parameters, PCR cycling parameters, signal ratio analysis, and signal ratio threshold.

In some embodiments, the kit further includes materials for DNA extraction from tissue or plasma.

The following examples are presented in order to more fully illustrate certain embodiments of the invention. They should in no way, however, be construed as limiting the broad scope of the invention. One skilled in the art can readily devise many variations and modifications of the principles disclosed herein without departing from the scope of the invention.

EXAMPLES

Example 1—Mutation Detection in DNA from Solid Tissues

Lung cancer tumor tissue samples (n=72, including adenocarcinoma, squamous cell carcinoma and small cell carcinoma) and normal lung tissue samples (n=25) were tested for KRAS G12 mutation by Sanger sequencing and by enzymatic restriction combined with real time (RT)-PCR according to the present invention.

DNA was extracted from the tissue samples using QIAamp® DNA mini kit. Because the native DNA sequence of KRAS around the G12 codon does not contain a restriction site, a pre-analytic PCR of 10 cycles that introduces a BstNI restriction site was performed, resulting with a modified sequence, using the following primers:

```
Forward
                                           (SEQ ID NO: 1)
5'-GGATCATATTCGTCCACAAAATG Reverse-
                                           (SEQ ID NO: 2)
5-TATAAACTTGTGGTAGTTGGACCT
```

The amount of DNA for the pre-analytic PCR was 4 ng.

The sequence around the G12 codon before and after introduction of the BstNI restriction site is as follows (the nucleotide that was modified to introduce the restriction site is marked in boldface, the introduced restriction site is underlined):

```
                                           (SEQ ID NO: 5)
  . . . GGA GCT GGT GGC GTA . . .

(SEQ ID NO: 6)
  . . . GGA CCT GGT . . .
```

The modified sequence is recognized by BstNI and expected to be cut extensively upon contact with the enzyme. In the presence of a mutation that changes one or more of the G nucleotides marked in italics the locus will no longer be recognized by BstNI and will not be cut.

Following introduction of the BstNI site, each DNA sample was subjected to digestion with BstNI. The digestion reaction (total volume 50 microliter) included 40 microliter of diluted (1:100) PCR product and BstNI in a digestion buffer. The digestion was carried out at 60° C. for 2 hours.

The digested DNA was subjected to quantitative RT-PCR to amplify a restriction locus containing the G12 codon and a control locus that does not contain a recognition sequence of BstNI and remains intact when the DNA sample is digested with this enzyme.

Sequence of the restriction locus (G12 codon is marked in boldface):

```
                                           (SEQ ID NO: 3)
TATAAACTTGTGGTAGTTGGACCTGGTGGCGTAGGCAAGAGTGCCTTG

ACGATACAGCTAATTCAGAATCATT TTGTGGACGAATATGATCC.
```

The restriction locus corresponds to position 25289485-25289577 on chromosome 12.

Sequence of the control locus:

```
                                           (SEQ ID NO: 4)
AGCAAGGTGAAGACTAACTTTTCTCTTGTACAGAATCATCAGGCTAAAT

TTTTGGCATT ATTTCAGTCC TTGGAGAC.
```

The control locus corresponds to position 121380844-121380921 on chromosome 7.

The amplification reaction (total volume 25 microliter) contained 10 microliters of the digested DNA, 0.2 µM primers, dNTPs and a reaction buffer. To enable detection of amplification products during amplification, fluorescently-labeled polynucleotide probes for each locus were added to the reaction (FAM and JOE labels, for the restriction and control loci, respectively). RT-PCR reactions were carried out in an ABI 7500 FastDx instrument with the following PCR program: 95° C. 10 min→45×(95° C. 15 sec→60° C. 1 min).

Figure 1B:
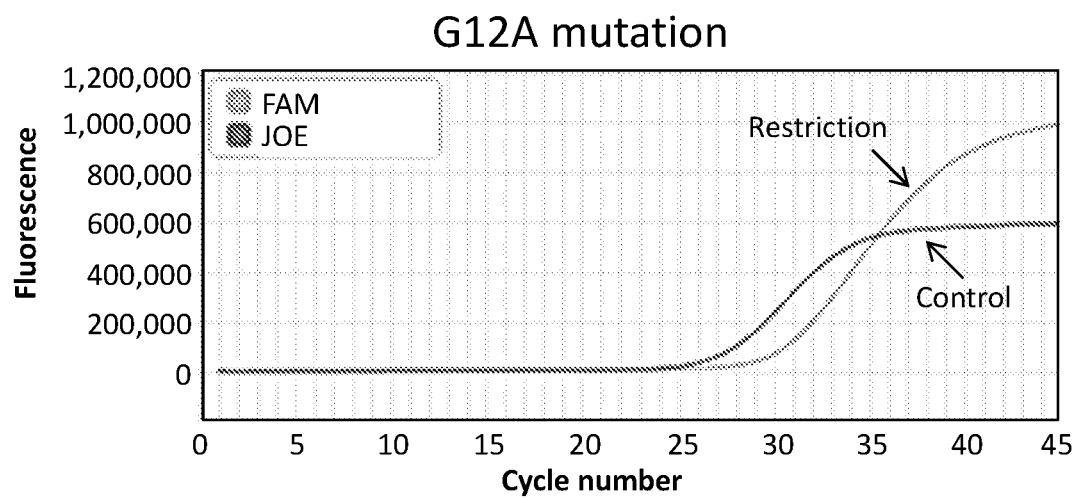
Figure 1C:
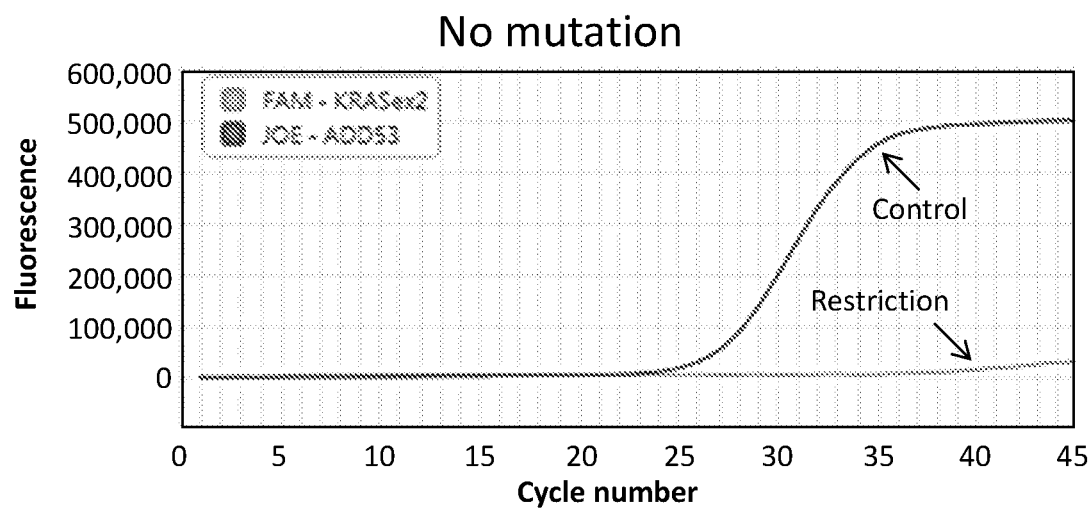
Figure 1D:
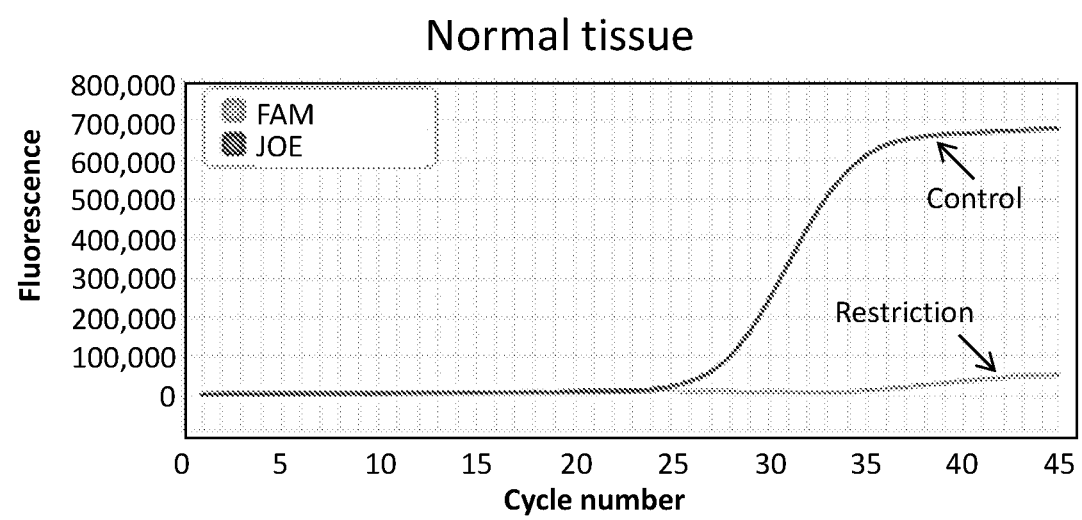

FIGS. 1A-1D show exemplary quantitative PCR plots, showing the change of fluorescent signals from the probes as a function of cycle number. The FIGURES show PCR plots of the restriction and control loci in DNA samples from cancerous lung tissues carrying a G12V mutation (FIG. 1A), a G12A mutation (FIG. 1B) or no G12 mutation (FIG. 1C), and in a DNA sample from a normal lung tissue (no G12 mutation) (FIG. 1D).

In the samples where a mutation is present, in which the restriction locus was no longer recognized by BstIN and therefore remained mostly intact when digested with the enzyme, the restriction locus was amplified with high efficiency. It rose roughly on the same cycle or 1-3 cycles later than the control locus (which was not cut at all).

In the samples with no mutation at G12 (cancerous or normal), the restriction locus was cut extensively by BstNI and hardly showed any amplification (FIG. 1C and FIG. 1D).

For each sample, ratios were calculated between the signal intensity of the restriction locus and the signal intensity of the control locus, as follows: the quantification cycle (Cq) was determined for the restriction locus and for the control locus. The Cq values were used in the following formula:

$$2^{(Cq\ of\ control\ locus - Cq\ of\ restriction\ locus)}$$

The numerical value obtained from this calculation represents the signal ratio between the restriction locus and the control locus.

In FIG. 1A—the Cq for the control locus is 28.3 and the Cq of the restriction locus is 27.8 therefore, the signal ratio is 1:0.7. This signal ratio is significantly higher than the threshold that was set (1:500, as will be explained in more detail below), indicating the existence of KRAS G12 mutation in the sample.

In FIG. 1B—the Cq for the control locus is 28.5 and the Cq of the restriction locus is 31.3 therefore, the signal ratio is 1:6.9. This signal ratio is also significantly higher than the threshold, indicating the existence of KRAS G12 mutation in the sample.

In FIG. 1C—the Cq for the control locus is 27.7. The restriction locus dose not rise above a minimum fluorescent threshold, therefore the Cq cannot be calculated and is determined as "infinity". For such cases the numerical value of the signal ratio is set to be 1:16000, significantly lower than the threshold (1:500). FIG. 1D represents a similar case, in which the Cq of the control locus is 28 and the Cq of the restriction locus is "infinity". Therefore, the signal ratio is 1:16000. Both samples are determined to be negative for a KRAS G12 mutation.

Results:

Sanger sequencing: no KRAS G12 mutation was identified in the normal lung tissue samples. 19% of the lung cancer tumor tissue samples were found to have KRAS G12 mutation.

Enzymatic restriction and RT-PCR assay: a signal ratio threshold of 1:500 was set, such that a signal ratio higher than 1:500 (e.g. 1:200) between the restriction locus and the control locus signifies presence of G12 mutation. The signal ratio threshold was set as 1:500 after analysis of a primary set of normal lung and lung tumor tissues, to obtain specificity above 95%. Based on the signal ratio data calculated for each sample, all lung cancer tumor tissue samples that were found to have KRAS G12 mutation by sequencing were also identified with G12 mutation. No KRAS G12 mutation was identified in the normal lung tissue.

Example 2—Mutation Detection in DNA from Plasma 105 plasma samples from control patients (without lung cancer) and 99 plasma samples from lung cancer patients were tested for KRAS G12 mutation as described in Example 1 above.

The signal ratio threshold for plasma derived DNA was set at 1:1000, such that a signal ratio higher than 1:1000 (e.g. 1:200) between the restriction locus and the control locus signifies presence of G12 mutation.

The signal ratio threshold was set as 1:1000 after testing a primary set of plasma samples from healthy (without lung cancer) and lung cancer patients, to minimize false positive cases (to obtain specificity of above 95%)—assuming that DNA from plasma samples of healthy people should not contain KRAS G12 mutation.

6% of the lung cancer plasma were identified as G12 mutation positive.

1% of the control plasma were identified as G12 mutation positive, indicating that 1% of the cases are false positive.

The foregoing description of the specific embodiments will so fully reveal the general nature of the invention that others can, by applying current knowledge, readily modify and/or adapt for various applications such specific embodiments without undue experimentation and without departing from the generic concept, and therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed chemical structures and functions may take a variety of alternative forms without departing from the invention.

The invention claimed is:

1. A method for detecting a cancer-related mutation in a DNA sample, the method comprising:
   (a) subjecting the DNA sample to digestion with a restriction endonuclease to obtain restriction endonuclease-treated DNA;
   (b) co-amplifying from the restriction endonuclease-treated DNA a restriction locus comprising a cancer mutation site and a control locus, thereby generating an amplification product for each locus,
   (c) calculating a ratio between signal intensities of the amplification products of the restriction locus and the control locus; and
   (d) detecting the cancer-related mutation in the DNA sample by comparing the ratio calculated in step (c) to a predefined threshold ratio.

2. The method of claim 1, wherein the DNA originates from a tumor tissue.

3. The method of claim 1, wherein the DNA originates from plasma.

4. The method of claim 1, wherein the control locus is a locus devoid of the recognition sequence of said restriction endonuclease.

5. The method of claim 1, wherein the DNA is native DNA, the restriction locus is a native restriction locus, and the restriction endonuclease is a methylation-insensitive restriction endonuclease whose recognition sequence comprises the cancer mutation site.

6. The method of claim 5, wherein the cancer-related mutation is selected from the group consisting of EGFR exon 19 deletion (E747-A750), EGFR L858 substitution, P53 H179 substitution, P53 G154 substitution, P53 R282 substitution, P53 R248 substitution, P53 R249 substitution and BRAF V600 substitution.

7. The method of claim 6, wherein the restriction endonuclease is selected from the group consisting of MseI (EGFR exon 19 deletion), MscI (EGFR L858 substitution), FatI (P53 H179 substitution), MspI (P53 G154 substitution, P53 R282 substitution, P53 R248 substitution), HaeIII (P53 R249 substitution) and TspRI (BRAF V600 substitution).

8. The method of claim 1, wherein the cancer mutation site is not naturally found within a recognition sequence of a restriction endonuclease, and wherein the DNA is a PCR product and the restriction locus is a restriction locus artificially-introduced into the DNA by said PCR.

9. The method of claim 8, wherein the cancer-related mutation is selected from the group consisting of a KRAS G12 substitution and an EGFR L858 substitution.

10. The method of claim 9, wherein the restriction endonuclease is selected from the group consisting of BtsIN (KRAS G12 substitution) and AluI (EGFR L858 substitution).

11. The method of claim 8, wherein the cancer-related mutation is a KRAS G12 substitution and the restriction endonuclease is BtsIN.

12. The method of claim 11, wherein the control locus is the locus set forth in SEQ ID NO: 4:

AGCAAGGTGAAGACTAACTTTTCTCTTGTACAGAATCATCAGGCTAAAT
TTTTGGCATT ATTTCAGTCC TTGGAGAC.

13. The method of claim 1, wherein the cancer-related mutation is selected from the group consisting of KRAS G12 substitution, EGFR exon 19 deletion (E747-A750), EGFR L858 substitution, P53 H179 substitution, P53 G154 substitution, P53 R282 substitution, P53 R248 substitution, P53 R249 substitution and BRAF V600 substitution.

14. The method of claim 1, wherein step (b) is performed using real-time PCR and the method further comprises adding fluorescent probes for assisting in detecting the amplification products of the restriction locus and the control locus.

15. The method of claim 14, wherein said calculating a ratio between the signal intensities of the amplification products of said restriction locus and the control locus comprises determining the quantification cycle (Cq) for each locus and calculating $2^{(Cq\ control\ locus - Cq\ restriction\ locus)}$.

16. A kit for detecting cancer-related mutations in a DNA sample, the kit comprising:
   at least one restriction endonuclease for digesting a DNA sample;
   a plurality of primer pairs for co-amplification of at least one restriction locus comprising a cancer mutation site and at least one control locus following digestion with the restriction endonuclease; and
   a computer readable medium storing a computer software that directs a computer processor to detect a cancer-related mutation in the DNA sample based on a comparison of a ratio of signal intensities of the restriction locus and the control locus following amplification to a predefined threshold ratio.

17. The kit of claim 16, wherein the computer software directs the computer processor to perform the following steps: determining signal intensities for the restriction locus and the control locus following their amplification; calculating a ratio between the signal intensities of the restriction locus and the control locus; comparing the calculated ratio to a predefined threshold ratio; and based on the comparison, outputting whether the DNA sample is positive for the cancer-related mutation.

18. The kit of claim 16, further comprising a plurality of polynucleotide probes for detecting amplification products of the at least one restriction locus and the at least one control locus.

19. A system for detecting cancer-related mutations in a DNA sample, the system comprising:
   at least one restriction endonuclease for digesting a DNA sample;
   a plurality of primer pairs for co-amplification of at least one restriction locus comprising a cancer mutation site and at least one control locus following digestion with the restriction endonuclease; and
   computer software stored on a computer readable medium that directs a computer processor to detect a cancer-related mutation in the DNA sample based on a comparison of a ratio of signal intensities of the restriction locus and the control locus following amplification to a predefined threshold ratio.

20. The system of claim 19, wherein the computer software directs the computer processor to perform the following steps: determining signal intensities for the restriction locus and the control locus following their amplification; calculating a ratio between the signal intensities of the restriction locus and the control locus; comparing the calculated ratio to a predefined threshold ratio; and based on the comparison, outputting whether the DNA sample is positive for the cancer-related mutation.

* * * * *